United States Patent [19]

Gölander et al.

[11] Patent Number: 4,565,740

[45] Date of Patent: Jan. 21, 1986

[54] SURFACE MODIFIED SOLID SUBSTRATE AND A METHOD FOR ITS PREPARATION

[75] Inventors: Carl-Gustaf Gölander, Stockholm; Rolf Larsson, Ekerö, both of Sweden

[73] Assignee: IRD-Biomaterial AB, Bromma, Sweden

[21] Appl. No.: 464,935

[22] Filed: Feb. 8, 1983

[30] Foreign Application Priority Data

Feb. 9, 1982 [SE] Sweden ................ 8200750

[51] Int. Cl.$^4$ .............. A61F 1/00; A61M 25/00; B01D 39/00; B32B 27/08
[52] U.S. Cl. .................. 428/409; 428/35; 428/339; 428/421; 428/474.4; 428/473; 428/515; 428/516; 428/532; 428/423.1; 428/446; 428/518; 428/457; 424/16; 424/31; 424/32; 424/33; 424/361; 424/35; 424/36; 424/180; 424/183; 210/500.2; 514/56; 514/59; 514/777
[58] Field of Search ............... 424/16, 31–36, 424/180, 183, 361; 260/6, 9, 17 A, 17 R, 77.5 Q; 428/35, 36, 339, 376, 398, 409, 411, 421, 473, 515, 532, 474.4, 423.1, 446

[56] References Cited

U.S. PATENT DOCUMENTS

| | | | |
|---|---|---|---|
| 3,616,935 | 11/1971 | Love et al. | 424/183 |
| 3,673,612 | 8/1972 | Merrill | 3/1 |
| 3,810,781 | 5/1974 | Eriksson et al. | 117/47 A |
| 4,001,583 | 1/1977 | Barrett | 250/303 |
| 4,118,485 | 10/1978 | Eriksson et al. | 424/183 |
| 4,229,838 | 10/1980 | Mano | 3/1.4 |
| 4,265,827 | 5/1981 | Eriksson et al. | 427/2 |
| 4,326,532 | 4/1982 | Hammar | 128/349 R |

FOREIGN PATENT DOCUMENTS

| | | |
|---|---|---|
| 365710 | 1/1974 | Sweden . |
| 400173 | 3/1978 | Sweden . |
| 79084463 | 10/1978 | Sweden . |
| 423863 | 6/1982 | Sweden . |
| 77082964 | 9/1982 | Sweden . |
| 2041377 | 1/1980 | United Kingdom . |

Primary Examiner—Patricia C. Ives
Attorney, Agent, or Firm—Burns, Doane, Swecker & Mathis

[57] ABSTRACT

A surface modified substrate, wherein the substrate carries a complex adsorbed thereto, which complex is of a polymeric cationic surfactant that contains primary amino nitrogens as well as secondary and/or tertiary amino nitrogens, and a dialdehyde that has 1–4 carbon atoms between the two aldehyde groups. To said complex there may additionally be bonded an anionic compound and optionally alternatingly additional cationic and anionic compounds. The modification primarily means that positive or negative charges can be imparted to the original substrate. Secondly, however, the point may be to utilize reactive groups in bonded cationic or anionic compounds.

The surface modified substrate is prepared by contacting the substrate with the polymeric cationic surfactant and the dialdehyde at such conditions that a complex is formed, which is adsorbed onto the substrate surface, and optionally continuing the ionic bonding with an anionic compound and possibly also alternatingly additional cationic and anionic compounds. The polymeric cationic surfactant and the dialdehyde are preferably utilized, separately or together, dissolved in a polar solvent, preferably water. The formation of the complex takes place at a pH-value above 8, whereupon the charges are preferably created at a pH-value below 7.

39 Claims, No Drawings

SURFACE MODIFIED SOLID SUBSTRATE AND A METHOD FOR ITS PREPARATION

TECHNICAL FIELD

The present invention relates to a surface modified substrate and to a method of surface modifying a substrate, i.e. to a method for the preparation of first-mentioned surface modified substrate. More specifically, the surface modification according to this invention generally implies that the substrate surface is furnished with ionic charges which can be of a positive or a negative character. The surface modification according to the invention means that such properties can be imparted to the substrate surface that anionic or cationic compounds can be adhered to the surface by means of ionic bonding so as to obtain a strong or a weak bonding strength. The choice between a strong or a weak ionic bonding is dependent on the desired use of the invention, as will be illustrated more in detail below. However, the applicability of the invention is not restricted to the utilization of charges imparted to the surface, but the primary objective can also be another one, e.g. the incorporation of chemically reactive groups such as amino groups on the substrate surface, which will also be further illustrated below. Finally, it should be noted that the invention is applicable to surface modification of non-charged as well as charged materials, although the utilization in connection with non-charged surfaces may be especially interesting in many cases.

In the field of surface treatment there is definitely a great need for methods for surface modification of commercially available standard materials for the purpose of achieving specific properties. As examples of desired properties one may mention improved wettability, altered adhesion characteristics, increased charge density or enhanced access to chemically reactive groups. One specific industrial problem has been to find a simple and versatile method for the preparation of charged surfaces. The availability of such a method is for instance a crucial prerequisite for the preparation of a heparinized surface according to Swedish Patent application No. 7708296-4. Said preparation is based on the adsorption of charged colloidal particles to a surface having opposite charges. Generally speaking, however, there is certainly a great need for methods which would allow surface attachment of biologically active substances in a number of therapeutic and analytic applications.

The invention is applicable to several types of solid substrates, e.g. steel such as stainless steel, glass or polymeric materials. Thanks to the fact that the invention in general implies an incorporation of charges onto the surface, it is of course primarily of special interest in connection with more or less non-charged materials or materials having insufficient surface charge density. In this context it should be noted that the expression "insufficient surface charge density" cannot be adequately defined, as it is the ultimate application that determines how high the surface charge density should be in each separate case. However, the invention is valuable in this respect as soon as a person skilled in the art can determine that the charge density of a substrate surface is inadequate for a specific purpose. However, it should be pointed out that it is useful also in those cases where the starting surface is already sufficiently charged. Thus, the principle of preparing modified substrate surfaces which are capable of accomplishing a strong or a weak bonding, by ionic or covalent bonding, to another substance, especially a polymeric anionic compound, can equally well be utilized in connection with a surface that carries electrical charges.

As hydrophobic materials of the polymeric material type belong to the group of more or less uncharged materials, the surfaces of which have previously been difficult to modify by any simple procedure, it is apparent that the invention will be of considerable value in connection with this type of materials. Among such materials reference can e.g. be made to some commonly used plastics material within the medical field such as polyvinyl chloride, polystyrene, polyurethanes, silicon rubber, polytetrafluoroethylene (Teflon ®) and not to forget the inexpensive and inert polyolefins, especially polyethylene but also polypropylene. Stainless steel is also a material that could be very useful in for instance the medical field if it were modified according to the invention.

PRIOR ART

In the above-mentioned Swedish Patent application No. 7708296-4 there are disclosed some methods for introducing surface charges, but without exception these carry various restrictions. Accordingly, an oxidation with concentrated sulphuric acid containing an oxidative agent can only be supplied to a few polymeric materials, and in addition thereto the method implies severe environmental problems. Specific methods for etching e.g. stainless steel or polyvinylchloride cannot be applied to any other materials.

GB-A-2 041 377 discloses bio- and blood compatible materials and methods but the disclosed principle differs from the one according to the present invention through the fact that according to said GB application one starts from a surface that has been provided with primary or secondary amino groups e.g. by swelling of an amino functional silating agent dissolved in an organic solvent, which is activated with a difunctional aldehyde or aryl halide, whereupon the biological substance is bonded to those aldehyde or aryl halide groups which are free to extend out of the surface. Thus, GB-A-2,041,377 does not disclose any method of obtaining surface bonded stable ionic complexes. Moreover, the method according to the present invention shows the advantage that no organic solvent is to be utilized.

SE Pat. No. 423,863 discloses the use of polyethylene imine for the manufacture of a vascular prosthesis. According to the disclosed method polyethylene imine is incorporated into pores of the material by allowing polyethylene imine to be fused into the pores, whereupon the polymer is made water insoluble by crosslinking. The amino groups are then quaternized and heparin is ionically bonded thereto. The applicability of the known method is obviously restricted to porous materials and it is not as simple and as generally applicable as the present invention.

DESCRIPTION OF THE INVENTION

According to the present invention a simple solution to the above schematically described problems is obtained, which solution is also extremely satisfying as to the obtained properties. This is achieved by those characteristics which are claimed in the claims to the surface modified substrate and the method, respectively.

The surface modified substrate according to the invention is thus characterized in that the non-modified substrate is provided with a complex of a polymeric cationic surfactant which is adsorbed thereto and which contains primary amino nitrogen atoms as well as secondary and/or tertiary amino nitrogen atoms, and of a dialdehyde which has 1–4 carbon atoms between the two aldehyde groups, and that to said complex there is optionally bonded, by ionic bonding, an anionic compound and optionally alternatingly additional cationic and anionic compounds, whereby the substrate surface can be positively or negatively charged.

The above-mentioned modified substrate according to the invention can be obtained from starting substrates that are non-charged as well as charged. However, if the starting substrate already carries negative charges an embodiment of the surface modified substrate according to the invention may be a substrate which is characterized in that the non-modified substrate carries adsorbed thereto a polymeric cationic surfactant that contains primary amino nitrogens as well as secondary and/or tertiary amino nitrogens and optionally ionically bonded to said surfactant a polymeric anionic compound preferably of the polysaccharide type, most preferably heparin.

Another embodiment of the surface modified solid substrate according to the invention in the case when the original non-modified substrate is already electrically charged is characterized in that the non-modified substrate carries adsorbed thereto a polymeric cationic surfactant that contains primary amino nitrogens as well as secondary and/or tertiary amino nitrogens, the surface carrying amino groups having such bonding properties that electrostatic bonding is essentially avoided if said primary amino groups are intended for covalent bonding of substances with a structurally related biological activity.

Polymeric cationic surfactants of the polyimine type are well-known agents per se for the treatments of cellulose in order to improve the retention of water. The favourable effect achieved thereby has been explained as a "jack-in-box" effect which is obtained by allowing the polymeric cationic surfactant to be adsorbed at an alkaline pH which imposes a relatively compressed structure to the molecule, whereupon it is enclosed by swelling when lowering the pH which makes the molecule expand.

The effect as to charge density and wettability that can be achieved by direct adsorption of a polymeric cationic surfactant to commonly available rigid polymeric materials have proven to be quite insufficient as judged from practical experiments. According to the present invention, however, it was unexpectedly discovered that much improved surfactant characteristics were imparted to the polymeric cationinc surfactants if they were allowed to react with said dialdehyde. An additional advantage is that the polymeric cationic surfactant acquires such qualities that it can exert a surprisingly strong electrostatic binding with polymeric anionic compounds.

A brief explanation of the resulting phenomena would be as follows, taking into account that the invention is by no means restricted to any special theory as to possible reaction mechanisms. The modification of the polymeric cationic surfactant imposes a strong increase of the hydrophobic interaction with the substrate surface by allowing the primary amino groups to be involved in binding to the dialdehyde which makes the molecule even less charged. Concomitantly the three dimensional structure of the polymeric surfactant becomes more rigid which creates favourable conditions for a strong fixation of polymeric anionic compounds via multiple electrostatic bonding to the remaining secondary and tertiary amino groups. The charged groups may then be utilized for an electrostatic coupling of anionic substances, e.g. heparin or dextran sulphate, as will be further illustrated below. Accordingly the bonding of such anionic molecules according to the present invention has shown to be surprisingly strong. This strong bonding or stability is for instance demonstrated by the fact that the anionic compound can still be detected after having incubated the complex with a buffer solution having a pH of 9. However, on the contrary, if the polymeric cationic surfactant has not been treated with glutardialdehyde, an instantaneous split of such a complex takes place at pH 9. As will be discussed below a polymeric anionic compound can alsio be firmly bonded by multiple electrostatic bonds via adsorption to a polymeric cationic surfactant if the latter is adsorbed at a pH of less than 7 to a surface with a high negative surface charge density.

According to a preferable embodiment of the invention the polymeric cationic surfactant contains at least 2, and preferably more than 2, primary amino groups in each polymer molecule. The preferred polymer would accordingly be referred to as a polyamine, but as the common nomenclature in the polymer field should be to denominate the polymer in respect of more or less dominating repeating units in the main chain, another terminology will be used below. The preferred "polyamine" function according to the invention should, however, remain implied.

Polyimines and polyamides are especially suitable polymeric cationic surfactants according to the invention, which substances thus carry secondary amino groups as dominating units in the polymer chain apart from projecting primary amino groups. In the case of polyimines there is, however, as is known also a considerable proportion of tertiary amino groups in the chain, while the secondary amino groups in the case of polyamides of course exist as amide bonds (—NCHO—).

An especially preferable type of polyimines is polyalkylene imines, especially polyethylene imine. Besides, a generally preferred group of the polymeric cationic surfactants is the group which has 1–6 carbon atoms between the imino nitrogen atoms in the polymer chains.

Examples of dialdehydes which are suitable according to the invention are succinic dialdehyde and glutardialdehyde, of which glutardialdehyde is especially preferable.

The initial adsorption of the complex obtained from the polymeric cationic surfactant and the dialdehyde results in a substrate which can be furnished with positive surface charges. In case the desired surface charge density is not accomplished through such a single layer, a charge of the opposite sign is required or chemically reactive groups are wanted on the substrate surface, one continues with conventional ionic bonding of an anionic compound in the first place and then possibly alternatingly additional cationic and anionic substances.

As to anionic compounds especially polymeric anionic compounds, preferably of the polysaccharide type, are of value for the performance of the invention with reference to the industrial applicability when using this type of compounds as well as with reference to the excellent binding of these compounds which is achieved according to the invention. Polysaccharides of particular interest are heparin, dextran sulphate, hyaluronic acid, and sulphated polyxylan.

A preferred embodiment of the surface modified substrate according to the invention is thus a substrate wherein a polymeric anionic compound is ionically bonded to the adsorbed complex of polymeric cationic surfactant and dialdehyde. Optionally additional layers of a polymeric anionic compound may be ionically bonded to the surface by means of intermediate ionically bonded cationic layers, which may comprise the described complex of the polymeric cationic surfactant and the dialdehyde or merely the polymeric cationic surfactant containing primary amino nitrogens as well as secondary and/or tertiary amino nitrogens. A very valuable application of said embodiment is the case when the polymeric anionic compound is heparin. Heparin is thus a well-known anticoagulant and the binding of heparin will be illustrated in more detail in the working examples below.

When heparin is used as the polymeric anionic compound the primary objective is of course to take advantage of the inherent characteristics of heparin rather than the negative charges which are created at the bonding of heparin. If, however, the main purpose is to create a negatively charged surface, it will be preferable to chose a polymeric anionic compound with a higher molecular weight than that of heparin (molecular weight 10,000 Daltons). Accordingly, the stability of the ionic complex increases with the molecular weight of the adsorbed anionic compound. Dextran sulphate is a particularly preferred compound in such a case, as this compound is available as a high molecular weight substance (molecular weight ~500,000 Daltons)

If a positively charged surface and/or a surface provided with chemically reactive primary amino groups are requested, a preferable embodiment of the invention means that to the adsorbed complex of polymeric cationic surfactant and dialdehyde there is ionically bonded a polymeric anionic compound, preferably of the polysaccharide type and for the above reason preferably dextran sulphate, and thereupon ionically bonded either the above-mentioned complex of the polymeric cationic surfactant and the dialdehyde or merely the polymeric cationic surfactant containing primary amino nitrogens as well as secondary and/or tertiary amino nitrogens. Thus, according to the latter alternative, in which only the polymeric cationic surfactant is used, the primary amino groups will be readily available for covalent bonding to suitable groups that are reactive with primary amino groups.

The invention also relates to a method for surface modifying a solid substrate by introducing ionic charges or reactive groups onto the substrate surface. The characteristic features of the method are that the substrate is contacted with a polymeric cationic surfactant which contains primary amino nitrogens as well as secondary and/or tertiary amino nitrogens, and a dialdehyde which has 1-4 carbon atoms between the two aldehyde groups, at such conditions that a complex is formed from the polymeric cationic surfactant and the dialdehyde, which complex is adsorbed onto the substrate surface, and if additional modification of the surface is required, that an anionic compound is ionically bonded to said complex carrying positive charges, and optionally that the ionic bonding is continued with alternating cationic and anionic compounds.

The method according to the invention is applicable to non-charged as well as charged substrate surfaces.

The most common situation from a practical point of view, however, is that the materials that would require a surface modification carry an insufficient surface charge density, which makes the method according to the invention especially valuable for non-charged or weakly charged surfaces.

However, another important aspect of the invention concerns the case when the original surface is already electrically charged and the effect of variation in pH at the adsorption of the polymeric cationic surfactant on the bonding strength of the complex formed during the subsequent adsorption of a polymeric anionic compound to the modified substrate, especially with primary amino groups.

Thus, the polymeric anionic compound is firmly bonded by multiple electrostatic bonds provided the polymeric cationic surfactant is adsorbed to a negatively charged surfact at a pH of less than 7. This means that the effect is similar to that achieved upon treatment of the polymeric cationic surfactant with dialdehyde. On the contrary, such a strong bonding can be avoided if the polymeric cationic surfactant is adsorbed to the negatively charged surface at a pH of more than 8. Apparently, it is essential to avoid strong fixation due to multiple electrostatic interaction when the substrate is going to be used for conjugation via covalent bonding to the primary amino groups of a substance, as e.g. heparin, having a biological activity which is closely related to its chemical structure.

Hence, according to an embodiment of the invention the method is characterized by contacting the substrate at a pH of less than 7, preferably within the range of 3-4, with a polymeric cationic surfactant that contains primary amino nitrogens as well as secondary and/or tertiary amino nitrogens, and optionally ionically bonding thereto, at a pH of less than 7, preferably within the range of 2-4, a polymeric anionic compound, preferably of the polysaccharide type, especially heparin.

According to another aspect of the invention a method is accomplished which is characterized by contacting the substrate at a pH above 8, preferably within the range of 8-10, with a polymeric cationic surfactant that contains primary amino nitrogens as well as secondary and/or tertiary amino nitrogens, whereby a substrate surface is obtained which carries amino groups having such bonding properties that electrostatic bonding is essentially avoided if said primary amino groups are intended for covalent bonding of substances with a structurally related biological activity.

As to the conditions for the formation of the above-mentioned complex and its adsorption to the substrate surface, they are preferably implemented by performing the first contact with the substrate while utilizing the polymeric cationic surfactant and the dialdehyde dissolved in a polar solvent, preferably water, at a pH above 8, and subsequently, if additional surface modification is to be performed, ionically bonding the anionic compound dissolved in a polar solvent, preferably water, at a pH of less than 7. The reaction with the dialdehyde may take place either in two steps, i.e. by dissolving the polymeric cationic surfactant and the dialdehyde separately in a polar solvent, the surface treatment being performed firstly with one solution and then with the other, or in one single step, the polymeric cationic surfactant being mixed with the dialdehyde in the solvent and the resulting reagent being adsorbed to the substrate surface. In the first-mentioned case the treatment of the surface is carried out at a pH above 8 in both steps, while in the latter case the mixing of the two components is performed at said pH above 8, but the subsequent adsorption to the substrate surface may well take place at a different pH.

When chosing a pH-value higher than 8, it is preferable to chose a value within the range of 8–12, especially 8–10 and most preferably around 9. As a pH-value less than 7 one should preferably choose a value within the range of 1–7, especially 2–4 and most preferably around 3.

If the additional surface modification with an anionic compound is not to be carried out or is to be carried out later on, the treatment with the polymeric cationic surfactant and the dialdehyde can be interrupted by rinsing the surface with the polar solvent, i.e. usually water, which thus generally means that the surface will acquire approximately a neutral pH-value. If there will be a need for positive charges later on, the surface is treated with a solution having an acidic pH, i.e. less than 7, preferably 1–7, especially 2–4 and most preferably around 3.

As concerns the aspects on the most preferred polymeric cationic surfactants and dialdehydes as well as on the substrate, which apply to the method according to the invention, the same is applicable as is described above in connection with the product, i.e. the surface modified substrate.

As to the treatment with the polymeric cationic surfactant and the dialdehyde in a polar solvent one should preferably use solutions having a concentration of the polymeric cationic surfactant of 0.0001–1, preferably 0.0001–0.005, percent by weight and 0.01–2, preferably 0.1–1, percent by weight of the dialdehyde.

According to yet another especially preferable embodiment of the method according to the invention NaCl is added to the solution of the anionic compound referred to above to increase the polarity of the solution, which should make the above described reorientation of the anionic compound even more efficient. The addition of NaCl should preferably be made to a final concentration of 0.01–1M, preferably about 0.15M.

In connection with the surface-modified substrate it was previuosly mentioned that polymeric anionic compounds, preferably of the polysaccharide type, would be particularly suitable as anionic compounds, and the same of course holds true also for the method according to the invention. Heparin, dextran sulphate, hyaluronic acid and sulphated polyxylan are thus the most suitable polysaccharides also in this case.

From the description above it should be evident that a preferred embodiment of the method according to the invention means that a polymeric anionic compound, preferably of the polysaccharide type, is ionically bonded to a complex of the polymeric cationic surfactant and the dialdehyde which is adsorbed to the substrate surface and that optionally the ionic bonding of the polymeric anionic compound is continued in additional layers. Accordingly the method results in the creation of a negatively charged surface which may sometimes be the primary objective, but another valuable aspect of this embodiment relates to the use of heparin as the polysaccharide, the inherent characteristics of heparin being of primary importance, in accordance with what has already been described above. When it comes to continued ionic bonding of the polymeric anionic compound in additional layers, it should be pointed out that this bonding can be accomplished either by means of the complex of the polymeric cationic surfactant and the dialdehyde or merely by using the polymeric cationic surfactant disclosed above.

A particularly interesting alternative of the last-mentioned embodiment comprises the ionic bonding of an anionic compound giving a high negative surface charge density, e.g. dextran sulphate, onto the surface-adsorbed complex of the polymeric cationic surfactant and the dialdehyde, and subsequently the ionic bonding of only the polymeric cationic surfactant at a pH of less than 7, preferably within the range of 3–4, and then the ionic bonding of the polymeric anionic compound at a pH of less than 7, preferably within the range of 2–4. By doing so it was unexpectedly discovered that the bonding of only the polymeric cationic surfactant results in the formation of a matrix of positive charges which can be ultilized for the formation of a stable ionic complex with a polymeric anionic compound. Thus, if for instance heparin is bonded to the polymeric cationic surfactant at such conditions a surface will be obtained to which heparin remains firmly bonded even on contact with blood plasma. This effect is surprising in comparison with the unstable complexes formed when the polymeric cationic surfactant is adsorbed to a weakly charged surface or at a pH value above 7.

Yet another important embodiment of the method according to the invention means that after the first adsorption of the complex of the polymeric cationic surfactant and the dialdehyde an anionic compound, preferably a polysaccharide, such as dextran sulphate, is bonded to the surface, and that additional ionic bonding is then carried out with the previously defined polymeric cationic surfactant only. Last-mentioned ionic bonding of merely the polymeric cationic surfactant may take place at a pH within the range of 2–10, the general rule being that a value within the lower part of the pH range is chosen when the primary objective is to create a surface with positive charges, whereas a pH value towards the alkaline side is chosen if the primary objective is to attach reactive primary amino groups to the surface rather than to introduce positive charges.

The invention will now be further illustrated by the following non-limitative examples.

EXAMPLES

As to the examples below, it should be noted that the percentages are by weight, unless expressly stated otherwise.

EXAMPLE 1

Polymin SN ® (BASF), which is a branched polyamine, was purified by precipitation in isopropanol, and the precipitate was then resuspended in water, and the remaining amount of isopropanol was evaporated by means of a thin film evaporator. A standard solution of 0.5 percent by weight was prepared.

Polyethylene tubings with an inner diameter of 1.8 mm and a length of 100 cm were prepared as follows:

A. Incubation for 10 minutes at room temperature with 0.5% Polymin SN solution at a pH of 9.0 followed by rinsing with water.

B. Treatment according to A, followed by treatment with 0.5% of glutardialdehyde in a borate buffer pH 9.0 for 10 minutes at room temperature, followed by rinsing with water.

C. Incubation for 10 minutes at room temperature with a 0.005% Polymin SN solution at pH 9.0, followed by rinsing with water.

D. Treatment according to C followed by treatment with 0.5% of glutardialdehyde in a borate buffer at pH 9.0 for 10 minutes at room temperature, followed by rinsing with water.

E. To a 0.5% solution of glutardialdehyde in a borate buffer at a pH of 9.0 there was added during agitation Polymin SN to a final concentration of 0.005%. Polyethylene tubings were incubated with a solution thus prepared for 10 minutes at room temperature, followed by rinsing with water.

Tubings from the groups A and C displayed poor wettability, while those from groups B, D, and E and displayed remarkedly good wettability.

In order to detect surface bonded positive charges, tubings from each group were tested as follows. At first tubings from each group were incubated with a water solution of heparin (20 IU/ml), pH 3, 55° C., 5 min) and then the tubings were carefully rinsed. The amount of surface bonded heparin was then assayed semiquantitatively in the following way.

The assay is based on the fact that thrombin is bound to heparin (or other polysaccharides), whereafter the amount of surface bound thrombin is measured by reaction (hydrolysis) with a thrombin-specific substrate, S-2238 (Kabi Diagnostica), the rate of reaction of which can readily be determined spectrophotometrically. From a practical point of view, the assay is carried out in such a way that 45 cm of the test tubing is first incubated for five minutes with 0.5 ml of bovine thrombin dissolved in a 4% albumin solution to a final concentration of 20 NIH units/ml (NIH=National Institute of Health). The surface is then carefully rinsed with saline and the remaining amount of thrombin is determined by incubation for 45 seconds with 1 ml of substrate S-2238 dissolved according to the instructions given by the manufacturer in a buffer solution at a pH of 8.4.

The amount of surface bound thrombin and, hence, also the amount of available heparin becomes proportional to the proportion of reacted substrate. The values are measured in absorbance units (abs. units), values below 0.004 abs.units/$cm^2$ indicating an insufficient and values of more than 0.020 abs.units/$cm^2$ indicating a sufficiently high binding capacity of the surface bonded heparin.

The following results were obtained:

| Group A | 0.001 abs.units/$cm^2$ |
|---|---|
| Group B | 0.028 abs.units/$cm^2$ |
| Group C | 0.000 abs.units/$cm^2$ |
| Group D | 0.027 abs.units/$cm^2$ |
| Group E | 0.027 abs.units/$cm^2$ |

The example shows that it is only the combination of the polymeric cationic surfactant and glutardialdehyde which gives the desired effect.

EXAMPLE 2

The following polymeric cationic surfactants were used:

(1) Polymin P ® (BASF): a linear polyethyleneamine,
(2) Kymene 557 H ® (Herkules Kemiska AB): a polyamide,
(3) Nalco 7134 ® (Nalco Chemical Company): a low molecular weight polyamine,
(4) Nalco 8102 ® (Nalco Chemical Company); a quaternized polyamine,
(5) Kymene 435 ® (Herkules Kemiska AB); a urea-formalderesinhyde,
(6) Polymin SN ® (BASF): a branched polyamine.

The substances were purified in the same way as was described for Polymin SN in example 1. Polyethylene tubings with a length of 45 cm and an inner diameter of 1.8 mm were used for the test.

A. Tubings were incubated for 10 minutes at room temperature with a 0.5% by weight water solution of each of said six polymeric cationic surfactants at a pH of 9.

The tubings were then rinsed in water, whereupon a treatment was performed with 0.5% glutaraldehyde in a borate buffer at pH 9 for 10 minutes at room temperature, followed by rinsing with water.

B. A 0.5% solution of glutardialdehyde in a borate buffer was prepared at pH 9, to which there was added each of the above-mentioned cationic surfactants during agitation to a final concentration of 0.015%. Tubings were incubated with each of the accordingly prepared solutions for 10 minutes at room temperature. Finally the tubings were rinsed in water.

Tubings from each of the groups A and B were examined with respect to water wettability, which was ranged from +(poor) to +++(complete). All tubings except A4, A5, and B4, B5 displayed wettability. (see Table).

In order to quantify the density of surface bonded positive charges, all tubings were incubated in heparin whereafter the amount of surface bonded heparin was determined according to the description given in Example 1. The results from such a test are given in the following table.

| Test | Substance | Chemical Characteristics | Wettability Gr. A | Wettability Gr. B | Abs. units/$cm^2$ Gr. A. | Abs. units/$cm^2$ Gr. B |
|---|---|---|---|---|---|---|
| 1 | Polymin P ® | Linear polyethyleneimine | ++ | ++ | 0.052 | 0.024 |
| 2 | Kymene 557 ® | Polyamide | ++ | ++ | 0.039 | 0.036 |
| 3 | Nalco 7134 ® | Low molecular weight polyamine | ++ | ++ | 0.038 | 0.035 |
| 4 | Nalco 8102 ® | Quaternized polyamine | − | − | 0.012 | 0.003 |
| 5 | Kymene 435 ® | Carbamide-formaldehyde resin | − | − | 0.026 | 0.024 |
| 6 | Polymin SN ® | Branched polyamine | ++ | ++ | 0.034 | 0.042 |

The test shows that a quaternized polyamine does not work as a reaction agent for preparing a surface modification substance. Ureaformaldehyde produces a doubtful effect. These substances do not carry those primary amino groups which are crucial for the reaction with glutardialdehyde. The test thus shows that merely cationic surfactants which contain both primary and secondary (and/or tertiary) amino nitrogens work as reaction agents for surface modification. The degree of branching is not critical, nor is the molecular weight of the polymer.

EXAMPLE 3

The following solutions were prepared:

A. A solution containing a complex of Polymin SN and glutaraldehyde at pH 9 was prepared according to Example 1E.

B. 100 mg of dextran sulphate was dissolved in 1 liter of water. Sodium chloride (NaCl) was added to a final concentration of 0.15 M. The pH was finally adjusted to 3.0.

Tubings or tubes of the following materials were used:

| | |
|---|---|
| Polyethylene | Polyurethane |
| PVC | Silicon rubber |
| Teflon ® | Stainless Steel |
| Polystyrene | Glass |

The different materials were treated firstly with A for 10 minutes at room temperature and after rinsing with water additionally with B for 10 minutes at 55° C. The procedure was repeated once on all materials except for silicon rubber for which the sequence was repeated four times.

The amount of surface bonded dextran sulphate was determined by assay of the amount of thrombin that had been adsorbed to the surface according to the method described in Example 1. The following results were obtained:

| Material | abs.units/cm$^2$ |
|---|---|
| Polyethylene | 0.035 |
| Polypropylene | 0.030 |
| PVC | 0.040 |
| Teflon ® | 0.020 |
| Polystyrene | 0.050 |
| Polyurethane | 0.020 |
| Silicon rubber | 0.020 |
| Stainless Steel | 0.078 |
| Glass | 0.070 |

The results show that all test surfaces can be modified according to the disclosed procedure.

EXAMPLE 4

During agitation Polymin SN was added to make up for a final concentration of 0.005% to a 0.5% solution of glutardialdehyde in a borate buffer at a pH of 9.0. Tubings of polyethylene were incubated with this solution for 5 minutes at room temperature, followed by rinsing with water. The tubings were then divided into three groups.

A. Incubation with a water solution of dextran sulphate having an average molecular weight of 10,000 (0.5 mg/ml, 0.15M NaCl, pH 3, 60° C., 5 min), followed by rinsing with water.

B. Incubation with a water solution of dextran sulphate having an average molecular weight of 500,000 (0.5 mg/ml, 0.15M NaCl, pH 3, 60° C., 5 min), followed by rinsing with water.

C. Incubation with a water solution of SP54 (sulphated polyxylan) (0.5 mg/ml, 0.15M NaCl, pH 3, 60° C., 5 min), followed by rinsing with water.

The tubings were then tested according to Example 1 with respect to adsorption of thrombin. The following results were obtained.

| | |
|---|---|
| A. | 0.027 abs.units/cm$^2$ |
| B. | 0.023 abs.units/cm$^2$ |
| C. | 0.026 abs.units/cm$^2$ |

EXAMPLE 5

Tubings of polyethylene were treated as follows:

A. Polymin SN was added to make up for a final concentration of 0.005% to a 0.5% solution of glutardialdehyde in a borate buffer at pH 9.0. Tubings were incubated with this solution for 5 minutes at room temperature, which was followed by rinsing with water. This step was followed by incubation with a water solution of heparin (20 IU/ml, pH 3, 0.15M NaCl, 60° C., 5 min), which was followed by rinsing first with a borate buffer at pH 9.0 and then with water.

B. Tubings from this group were treated exactly as according to A, but the sequence comprising a Polymin-glutar solution followed by a heparin solution was carried out twice in total.

The tubings were then tested with respect to thrombin adsorption according to the description given in Example 1. The following results were obtained:

| | |
|---|---|
| A. | 0.038 abs.units/cm$^2$ |
| B. | 0.039 abs.units/cm$^2$ |

In a separate test the heparin surfaces were tested with respect to adhesion of platelets. The tubings were circulated with fresh human citrated blood for 20 minutes and then rinsed in a standardized way with saline. Eventually ATP (adenosine triphosphate) was extracted from the adhered platelets with a buffer solution and the amount of ATP was determined. The following results were obtained.

| | |
|---|---|
| Untreated polyethylene | $1930 \cdot 10^{-11}$ mmol of ATP/cm$^2$ |
| Group A | $818 \cdot 10^{-11}$ mmol of ATP/cm$^2$ |
| Group B | $20 \cdot 10^{-11}$ mmol of ATP/cm$^2$ |

The results show that the substrate surface (polyethylene) was completely covered by a platelet repellant heparin layer by the procedure based on two sequences (case B).

EXAMPLE 6

Tubings of polyethylene were treated as follows.

Polymin SN was added to make up for a final concentration of 0.005% to a 0.5% solution of glutaraldehyde in a borate buffer at pH 9.0. Tubings were incubated with this solution for 5 minutes at room temperature which was followed by rinsing with water. Then an incubation was carried out with a water solution of high molecular weight dextran sulphate (average molecular weight of 500,000, 0.1 mg/ml, pH 3, 0.15M NaCl, 50° C., 5 min) and the tubings were then rinsed with water. The described sequence was repeated once. A treatment was then made with a 0.05% water solution of Polymin SN at pH 3.5 for 5 minutes at room temperature, followed by rinsing with water. Finally a treatment was made with a water solution of hyaluronic acid (0.1 mg/ml, pH 3, 0.15M NaCl, 50° C., 5 min). The same procedure was exactly repeated while using heparin (20 IU/ml, pH3, 0.15M NaCl, 50° C., 5 min) instead of hyaluronic acid. The tubings were then divided into two groups, the first of which was rinsed only with water and the second one first with a buffer solution at pH 9.0 and then abundantly with water.

The tubings were then tested in respect of uptake of thrombin according to the description given in Example 1. The following results were obtained.

|  | Water rinsing only abs.units/cm$^2$ | Incubation at pH 9.0 followed by rinsing with water abs.units/cm$^2$ |
| --- | --- | --- |
| Hyaluronic acid | 0.034 | 0.033 |
| Heparin | 0.032 | 0.034 |

This example shows that hyaluronic acid and heparin were firmly attached to the surface.

EXAMPLE 7

Tubings of polyethylene were treated as follows.

Polymin SN was added to make up for a final concentration of 0.005% to a 0.5% solution of glutaraldehyde in a borate buffer at pH 9.0. The tubings were incubated with this solution for 5 minutes at room temperature followed by rinsing with water. An incubation was then made with a water solution of high molecular weight dextran sulphate (average molecular weight of 500,000, 0.1 mg/ml, pH 3, 0.15M NaCl, 50° C., 5 min), whereupon the tubings were rinsed with water. The described sequence was repeated once more. A treatment was then made with a 0.05% water solution of Polymin SN at pH 9.0 for 5 minutes at room temperature, which was followed by rinsing with water. To the substrate modified accordingly heparin was linked by using a heparin that had been furnished with a free terminal aldehyde group by means of diazotization. To that effect the tubings were incubated with a water solution (pH 3.9, 0.15M NaCl) containing 0.25 mg/ml of diazotized heparin and 0.025 mg/ml of sodium cyanoborohydride for two hours at 50° C. The treatment was terminated by a careful rinsing with water.

The heparinized tubings were subsequently tested in the same way as was described in Example 5, and the following results were obtained.

1. An uptake of thrombin without prior exposure to plasma resulted in 0.032 abs.units/cm$^2$.

The method for measuring surface-bonded thrombin can also be applied to the testing of the non-thrombogenic character of a surface. For this purpose the test surface is first exposed to human citrated plasma for 60 minutes in order to establish the relevant protein adsorbate on the surface. After this exposure the test items are separated into two groups. The first group (I) is rinsed only with saline but the other group is also incubated with defibrinogenated plasma (i.e. plasma that has been depleted of fibrinogen and is therefore not capable of forming a clot). The criteria to be met by a non-thrombogenic surface are that the uptake of thrombin, which is measured as described, should amount to at least 0.020 abs.units/cm$^2$ in group I and should be less than 0.0020 abs.units/cm$^2$ in group II. The following results were obtained.

| Group (I) | Group (II) |
| --- | --- |
| Rinsing with saline only | Saline + defibrinogenated plasma |
| 0.029 abs.units/cm$^2$ | 0.0004 abs.units/cm$^2$ |
| 3. Platelet adhesion test: | |
| Untreated polyethylene | $1750 \cdot 10^{-11}$ mmol ATP/cm$^2$ |
| Heparinized polyethylene | $29 \cdot 10^{-11}$ mmol ATP/cm$^2$ |

This example shows that the heparinized surface has excellent non-thrombogenic characteristics.

The example also illustrates the general method, which has been described above and which comprises a surface modification for the purpose of creating a substrate with free primary amino groups, which can be covalently linked to groups that react with primary amino groups.

In this case, the binding takes place to heparin which has been degraded by diazotization to form a substance fragment with a free terminal aldehyde group. This aldehyde group then reacts with the primary amino groups of the substrate to form a Schiff's base, which is converted to a secondary amine by reduction.

The conjugate that is obtained by the coupling can accordingly be defined as a conjugate consisting of a 1-deoxy-2,5-anhydromannitol residue, which forms the terminal unit of a polysaccharide, which is in this case derived from heparin, and which is covalently bound in the 1-position to an amino group attached to the substrate.

The diazotization of heparin is preferably carried out in a water solution by means of a suitable diazotization agent, e.g. a nitride, such as sodium nitrite in an acid solution or butylnitrite. The diazotization agent is generally an agent capable of forming NO+ions.

The reaction between the aldehyde group and the amino group of the substrate can take place in water at a pH of 3–7 or within the same pH range in a suitable organic solvent, e.g. formamide or dimethyl sulphoxide.

As to the reduction, finally, it is carried out by means of a suitable reduction agent, e.g. a cyanoborohydride, preferably of an alkali metal, such as sodium, potassium or lithium, for the formation of stable secondary amines.

The reaction between the aldehyde group of the modified heparin and the amino group of the substrate can be illustrated by the following reaction formula:

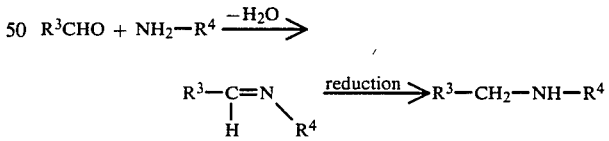

EXAMPLE 8

Polyethylene tubings were filled with concentrated sulphuric acid containing potassium permanganate (2 g/l) and incubated for two minutes and then carefully rinsed with pure water. This treatment results in a high negative surface charge by the introduction of carboxylic and sulphate groups. The tubings were then provided with surface bonded amino groups according to two different treatments.

A. Incubation for five minutes at room temperature with a 0.01% water solution of polyethyleneimine at a pH of 3.0 followed by rinsing with water.

B. Incubation for five minutes at room temperature with a 0.01% water solution of polyethyleneimine at a pH of 9.0 followed by rinsing with water.

The aminated surfaces were then treated with heparin according to the following two groups.

Ionic bonding: Incubation for two hours at 50° C. with a water solution containing unmodified heparin (0.2 mg/ml) and sodium chloride (0.15M) at a pH of 3.5 followed by extensive rinsing with water.

Covalent bonding: Incubation for two hours at 50° C. with a water solution containing partially degraded heparin (0.2 mg/ml), sodium cyanoborohydride (0.02 mg/ml) and sodium chloride (0.15M) at a pH of 3.5 followed by rinsing with water.

The tubings were then tested for their capacity of adsorbing thrombin according to example 1. Half of the tubings of each group were rinsed with a borate buffer solution having a pH of 9 before testing. The following results were obtained.

| Type of Surface | Type of rinsing prior to exposure to thrombin | |
|---|---|---|
| | $H_2O$ | $H_2O$ + Buffer pH 9 |
| A - ionic bonding | 0.030 | 0.030 |
| A - covalent bonding | 0.032 | 0.031 |
| B - ionic bonding | 0.00 | 0.00 |
| B - covalent bonding | 0.034 | 0.035 |

This test shows that heparin is firmly bonded to the surface of type A not only via covalent bonding but as well via ionic bonding. On the B surface, however, the ionic bonding is so weak as to allow heparin to be washed away already during exposure to thrombin. Hence, it is only via the covalent bonding that heparin can be firmly attached to this surface.

The tubings were next tested for their non-thrombogenic character by measuring the adsorption and subsequent inhibition of thrombin according to the description given in Example 7. The following results were obtained.

| Type of Surface | Surface bonded thrombin activity expressed as abs.units/cm$^2$ after exposure to: | |
|---|---|---|
| | Saline Group I | Defibrinogenated Plasma, Group II |
| A - ionic bonding | 0.031 | 0.030 |
| A - covalent bonding | 0.032 | 0.029 |
| B - ionic bonding | 0.00 | — |
| B - covalent bonding | 0.033 | 0.00 |

This test shows that both ionic and covalent bonding of heparin to the A surface results in a thrombogenic character due to the fact that the adsorbed thrombin will not be inhibited on exposure to plasma. It is only heparin which has been linked to the B surface via covalent bonding that exerts a biological activity in terms of inhibition of surface bonded thrombin.

This example clearly illustrates the crucial importance of choosing the appropriate substrate for a successful immobilization of heparin, which means that the active sequence responsible for the biological activity of heparin has not been immobilized but is free to interact with plasma constituents.

We claim:

1. A surface modified solid substrate, wherein the substrate carries a complex adsorbed thereto which complex is of a polymeric cationic surfactant and a dialdehyde, the surfactant containing primary amino nitrogens as well as secondary and/or tertiary amino nitrogens, and the dialdehyde having 1–4 carbon atoms between the two aldehyde groups.

2. A surface modified substrate according to claim 1 wherein the polymeric cationic surfactant contains at least two primary amino groups in each polymer molecule.

3. A surface modified substrate according to claim 2, wherein the polymeric cationic surfactant is selected from the group consisting of polyimines and polyamides.

4. A surface modified substrate according to claim 1, wherein the polymeric cationic surfactant is a polyalkyleneimine.

5. A surface modified substrate according to claim 1, wherein the polymeric cationic surfactant has 1–6 carbon atoms between the amino nitrogen atoms in the polymer molecule.

6. A surface modified substrate according to claim 1, wherein the polymeric cationic surfactant is a polyethyleneimine.

7. A surface modified substrate according to claim 1, wherein the dialdehyde is glutardialdehyde.

8. A surface modified substrate according to claim 1, wherein the substrate is selected from the group consisting of stainless steel, glass or a polymeric material selected from polyvinylchloride, polyurethanes, silicon rubber, polytetrafluoroethylene, polystyrene, and polyolefins.

9. A surface modified substrate according to claim 8, wherein the substrate is polyethylene.

10. A surface modified substrate according to claim 1, wherein there is ionically bonded to the adsorbed complex of polymeric cationic surfactant and dialdehyde, a polymeric anionic compound.

11. A surface modified substrate according to claim 10, wherein additional layers of the polymeric anionic compound are ionically bonded to the surface by means of intermediate ionically bonded layers of said complex of the polymeric cationic surfactant and the dialdehyde or the polymeric cationic surfactant alone, which contains primary amino nitrogens as well as secondary and/or tertiary amino nitrogens.

12. A surface modified substrate according to claim 1, wherein there is ionically bonded to the adsorbed complex of polymeric cationic surfactant and dialdehyde a polymeric anionic compound, and thereupon, ionically bonded as well, said complex of the polymeric cationic surfactant and the dialdehyde, or the polymeric cationic surfactant alone, which contains primary amino nitrogens as well as secondary and/or tertiary amino nitrogens.

13. A surface modified substrate according to, claims 10 or 12, wherein the polymeric anionic compound is a polysaccharide selected from the group consisting of heparin, dextran sulphate, hyaluronic acid and sulphated polyxylan.

14. A surface modified substrate according to claim 10, wherein the polymeric anionic compound is heparin.

15. A surface modified substrate according to claim 12, wherein the polymeric anionic compound is dextran sulphate.

16. A surface modified substrate according to claim 1, wherein there is bonded to said complex, via ionic binding, an anionic compound.

17. A surface modified substrate according to claim 1, wherein additional cationic and anionic compounds are alternatingly bonded to said complex, whereby the modified substrate is positively or negatively charged.

18. A method of surface modifying a solid substrate by introducing ionic charges on the substrate surface, which comprises contacting the substrate with a polymeric cationic surfactant which contains primary amino nitrogens as well as secondary and/or tertiary amino nitrogens, and a dialdehyde which contains 1-4 carbon atoms between the two aldehyde groups, at such conditions that a complex of the polymeric cationic surfactant and the dialdehyde is formed, which complex is adsorbed to the substrate surface.

19. A method according to claim 18, which comprises performing the first contact with the substrate while using the polymeric cationic surfactant and the dialdehyde dissolved separately or together in a polar solvent, and at a pH-value higher than 8, the treatment being carried out with separate solutions in two steps or with a mixture in one step, and then making a rinsing operation with the polar solvent.

20. A method according to claim 19, which comprises choosing as the pH-value higher than 8 a value within the range of 8-12.

21. A method according to claim 18, wherein the polymeric cationic surfactant contains at least two primary amino groups in each polymer molecule.

22. A method according to claim 21, wherein the polymeric cationic surfactant is selected from the group consisting of polyimines and polyamides.

23. A method according to claims 18 or 19, wherein the polymeric cationic surfactant is a polyalkyleneimine.

24. A method according to claim 18, wherein the polymeric cationic surfactant has 1-6 carbon atoms between the amino nitrogen atoms in the polymer molecule.

25. A method according to claims 18 or 19, wherein the polymeric cationic surfactant is a polyethyleneimine.

26. A method according to claims 18 or 19, wherein the dialdehyde is glutardialdehyde.

27. A method according to claims 18, or 19, wherein the substrate is selected from the group consisting of stainless steel, glass or a polymeric material selected from polyvinylchloride, polyurethanes, silicon rubber, polytetrafluoroethylene, polystyrene and polyolefins.

28. A method according to claim 19, wherein the concentration of the solution with respect to the polymeric cationic surfactant is 0.0001-1, percent by weight, and with respect to the dialdehyde 0.01-2, percent by weight.

29. A method according to claim 28, which comprises adding NaCl to the solution of the anionic compound to make up for a final concentration of 0.01-1M, to increase the polarity of the solution.

30. A method according to claim 18, which comprises ionically bonding a polymeric anionic compound to the complex of the polymeric cationic surfactant and the dialdehyde adsorbed to the substrate surface.

31. A method according to claim 30, which comprises ionically bonding dextran sulphate to the complex of the polymeric cationic surfactant and the dialdehyde adsorbed to the substrate surface, and then ionically bonding the polymeric cationic surfactant at a pH of less than 7, and subsequently ionically bonding the polymeric anionic compound at a pH of less than 7.

32. A method according to claim 18, which comprises ionically bonding to the complex of the polymeric cationic surfactant and the dialdehyde, an anionic compound, to the surface, and subsequently performing additional ionic bonding, at a pH within the range of 2-10, with the polymeric cationic surfactant containing primary amino nitrogens as well as secondary and/or tertiary amino nitrogens.

33. A method according to claim 30, wherein the polysaccharide is selected from the polymeric anionic compound is a group consisting of heparin, dextran sulphate, hyaluronic acid and sulphated polyxylan.

34. A method according to claim 31, wherein the polymeric anionic compound is heparin.

35. A method according to claim 18, wherein an anionic compound is ionically bound to said complex exhibiting positive charges.

36. A method according to claim 19, wherein the polar solvent is adjusted to a pH of less than 7.

37. A method according to claim 36, wherein the pH is within the range of 1-7.

38. A method according to claim 27, wherein the substrate is polyethylene.

39. A method according to claim 30, wherein ionic bonding of the polymeric anionic compound is continued to make up additional layers, said complex of the polymeric cationic surfactant and the dialdehyde or solely the polymeric cationic surfactant that contains primary amino nitrogens as well as secondary and/or tertiary amino nitrogens being ionically bonded between the ionic layers.

* * * * *